US011786221B2

(12) United States Patent
Erkamp et al.

(10) Patent No.: US 11,786,221 B2
(45) Date of Patent: Oct. 17, 2023

(54) ULTRASOUND INTERVENTIONAL DEVICE LOCATION DETERMINATION USING SIGNALS REPETITIVE NOISE AND OFFSET INFORMATION

(71) Applicant: KONINKLIJKE PHILIPS N.V., Eindhoven (NL)

(72) Inventors: Ramon Erkamp, Swampscott, MA (US); Alvin Chen, Cambridge, MA (US); Shyam Bharat, Arlington, MA (US); Kunal Vaidya, Boston, MA (US); Francois Guy Gerard Marie Vignon, Andover, MA (US); Ameet Kumar Jain, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 288 days.

(21) Appl. No.: 17/044,349

(22) PCT Filed: Apr. 2, 2019

(86) PCT No.: PCT/EP2019/058228
§ 371 (c)(1),
(2) Date: Oct. 1, 2020

(87) PCT Pub. No.: WO2019/192981
PCT Pub. Date: Oct. 10, 2019

(65) Prior Publication Data
US 2021/0100531 A1 Apr. 8, 2021

Related U.S. Application Data
(60) Provisional application No. 62/651,489, filed on Apr. 2, 2018.

(51) Int. Cl.
A61B 8/00 (2006.01)
A61B 8/08 (2006.01)
A61B 8/12 (2006.01)

(52) U.S. Cl.
CPC .......... *A61B 8/5269* (2013.01); *A61B 8/0841* (2013.01); *A61B 8/12* (2013.01); *A61B 8/4254* (2013.01)

(58) Field of Classification Search
CPC ....... A61B 8/5269; A61B 8/0841; A61B 8/12; A61B 8/4254
See application file for complete search history.

(56) References Cited

U.S. PATENT DOCUMENTS 9,704,240 B2   7/2017 Lam et al.
2011/0196259 A1   8/2011 Gianchandani et al.
(Continued)

FOREIGN PATENT DOCUMENTS

JP   2009251441 A   10/2009
WO  2015155649 A1   10/2015

OTHER PUBLICATIONS

Xia, W., West, S., Finlay, M., Mari, J.M., Ourselin, S., et. al., "Looking beyond the imaging plane: 3D needle tracking with a linear array ultrasound probe." Scientific Reports. (Year: 2017).*
Huang et al: "Imaging Artifacts of Medical Instruments in Ultrasound-Guided Interventions"; 2007, American Institute of Ultrasound in Medicine, pp. 1304-1322.
(Continued)

Primary Examiner — Serkan Akar
Assistant Examiner — Amal Aly Farag

(57) ABSTRACT

A system for determining location of an interventional medical device within a patient includes a controller that controls an ultrasound probe to emit imaging beams at different times and angles relative to the ultrasound probe. The system also includes an interventional medical device with an attached sensor that receives the imaging beams together with repetitive noise. The controller further identi-
(Continued)

fies the repetitive noise received at the sensor, including identifying the rate at which the repetitive noise is repeated and identifying the times at which the repetitive noise is received at the sensor. The controller further offsets the repetitive noise in signals received at the sensor by interpolating the signals based on the imaging beams. The controller determines the location of the interventional medical device based on the offset signals.

10 Claims, 13 Drawing Sheets

(56) References Cited

U.S. PATENT DOCUMENTS

| 2016/0038119 A1* | 2/2016 | Desjardins | A61B 8/4444 600/424 |
| 2017/0148161 A1* | 5/2017 | Griffin | A61B 5/0066 |

OTHER PUBLICATIONS

Lu et al: "A New Sensor Technology for 2D Ultrasound-Guided Needle Tracking"; MICCAI 2014, Part II, LNCS 8674, pp. 389-396, 2014.

Mung et al: "A Non-Disruptive Technology for Robust 3D Tool Tracking for Ultrasound-Guided Interventions"; MICCAI 2011, Part 1, LNCS 6891, pp. 153-160, 2011.

PCT/EP2019/058228 ISR & WO, Jun. 25, 2019, 16 Pages.

* cited by examiner

First focal depth:
Raw noise level (max) : 454.72 [mV]
SNR pre filter (max signals) : -10.63 [dB]
dB suppression noise : 23.08 [dB]

Signal level (max) : 133.63 [mV]
SNR after filter (max signals) : 12.44 [dB]

ULTRASOUND INTERVENTIONAL DEVICE LOCATION DETERMINATION USING SIGNALS REPETITIVE NOISE AND OFFSET INFORMATION

CROSS-REFERENCE TO PRIOR APPLICATIONS

This application is the U.S. National Phase application under 35 U.S.C. § 371 of International Application No. PCT/EP2019/058228, filed on Apr. 2, 2019, which claims the benefit of U.S. Provisional Patent Application No. 62/651,489, filed on Apr. 2, 2018. These applications are hereby incorporated by reference herein.

BACKGROUND

In ultrasound imaging, the visibility of an interventional medical device such as a needle is often poor due to the specular nature of the needle surface that reflects imaging beams away. To alleviate this problem some needle manufacturers have produced needles with special echogenic coatings, but the improvement in visibility is limited. Algorithms that use multiple imaging beams from different angles have been developed, but improvement is again limited and such a strategy is primarily suited only for linear arrays. Both strategies do not help when the needle is inserted perpendicular to the imaging plane or the needle path has a small offset relative to the imaging plane.

One solution to improve visibility for interventional medical devices such as needles as well as catheters is to add passive ultrasound sensors (e.g., PZT, PVDF, copolymer or other piezoelectric material) near the tip of the interventional medical device. A passive ultrasound sensor is an acoustic pressure sensor, and these passive ultrasound sensors are used in "InSitu" mechanisms to determine location of the passive ultrasound sensor. The position of a passive ultrasound passive sensor is estimated in the field of view (FOV) of a diagnostic ultrasound B-mode image by analyzing the signal received by the passive ultrasound sensor as imaging beams from an ultrasound probe sweep the field of view. Time-of-flight measurements provide the axial/radial distance of the passive ultrasound sensor from an imaging array of the ultrasound probe, while amplitude measurements and knowledge of the imaging beam firing sequence provide the lateral/angular position of the passive ultrasound sensor. This information is used to calculate sensor position relative to the ultrasound image with positional accuracy exceeding 0.5 mm, even under conditions where the needle is not visible in the ultrasound image.

FIG. 1 illustrates a known system for tracking an interventional medical device using a passive ultrasound sensor. In FIG. 1, an ultrasound probe 102 emits an imaging beam 103 that sweeps across a passive ultrasound sensor 104 on a tip of an interventional medical device 105. An image of tissue 107 is fed back by the ultrasound probe 102. A location of the passive ultrasound sensor 104 on the tip of the interventional medical device 105 is provided as a tip location 108 upon determination by a signal processing algorithm. The tip location 108 is overlaid on the image of tissue 107 as an overlay image 109. The image of tissue 107, the tip location 108, and the overlay image 109 are all displayed on a display 100.

Noise/interference spikes in the signal received at the passive ultrasound sensor can prevent the proper localization of the passive ultrasound sensor due to generating false peaks. A method is described to reduce the interference, for a class of interference signals that is repetitive in nature.

SUMMARY

According to an aspect of the present disclosure, a controller for reducing noise in an ultrasound environment includes a memory that stores instructions; and a processor that executes the instructions. When executed by the processor, the instructions cause the controller to execute a process that includes controlling emission, by an ultrasound probe, of multiple imaging beams each at a different combination of time of emission and angle of emission relative to the ultrasound probe. The process executed by the controller also includes identifying repetitive noise from a first source received with the multiple imaging beams at a sensor on an interventional medical device, including a rate at which the repetitive noise from the first source repeats and times at which the repetitive noise from the first source is received. The process executed by the controller also includes interpolating signals based on the multiple imaging beams received at the sensor to offset the repetitive noise from the first source at the times at which the repetitive noise from the first source is received.

According to another aspect of the present disclosure, a method for reducing noise in an ultrasound environment includes controlling emission, by an ultrasound probe, of multiple imaging beams each at a different combination of time of emission and angle of emission relative to the ultrasound probe. The method also includes identifying repetitive noise from a first source received with the multiple imaging beams at a sensor on an interventional medical device, including a rate at which the repetitive noise from the first source repeats and times at which the repetitive noise from the first source is received. The method also includes interpolating signals based on the multiple imaging beams received at the sensor to offset the repetitive noise from the first source at the times at which the repetitive noise from the first source is received.

According to yet another aspect of the present disclosure, a system for reducing noise in an ultrasound environment includes a sensor, an ultrasound probe, and a controller. The sensor is at a location on an interventional medical device. The ultrasound probe emits multiple imaging beams each at a different combination of time of emission and angle of emission relative to the ultrasound probe. The controller includes a memory that stores instructions and a processor that executes the instructions. When executed by the processor, the instructions cause the controller to execute a process that includes controlling emission, by the ultrasound probe, of the multiple imaging beams. The process executed by the controller also includes identifying repetitive noise from a first source received with the multiple imaging beams at the sensor on an interventional medical device, including a rate at which the repetitive noise from the first source repeats and times at which the repetitive noise from the first source is received. The process executed by the controller also includes interpolating signals based on the multiple imaging beams received at the sensor to offset the repetitive noise from the first source at the times at which the repetitive noise from the first source is received.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
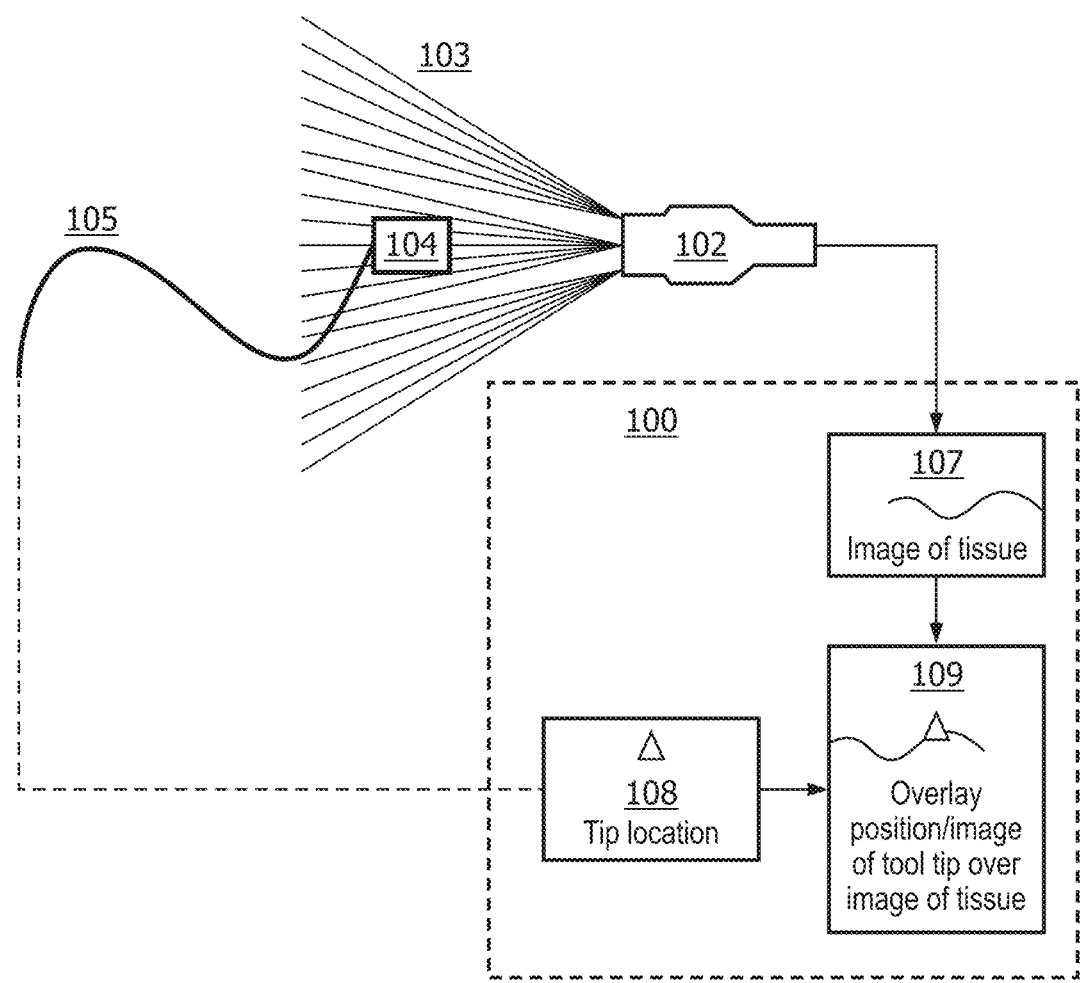
FIG. 1 illustrates a known system for interventional medical device tracking using a passive ultrasound sensor, in accordance with a representative embodiment.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

Figure 2A:
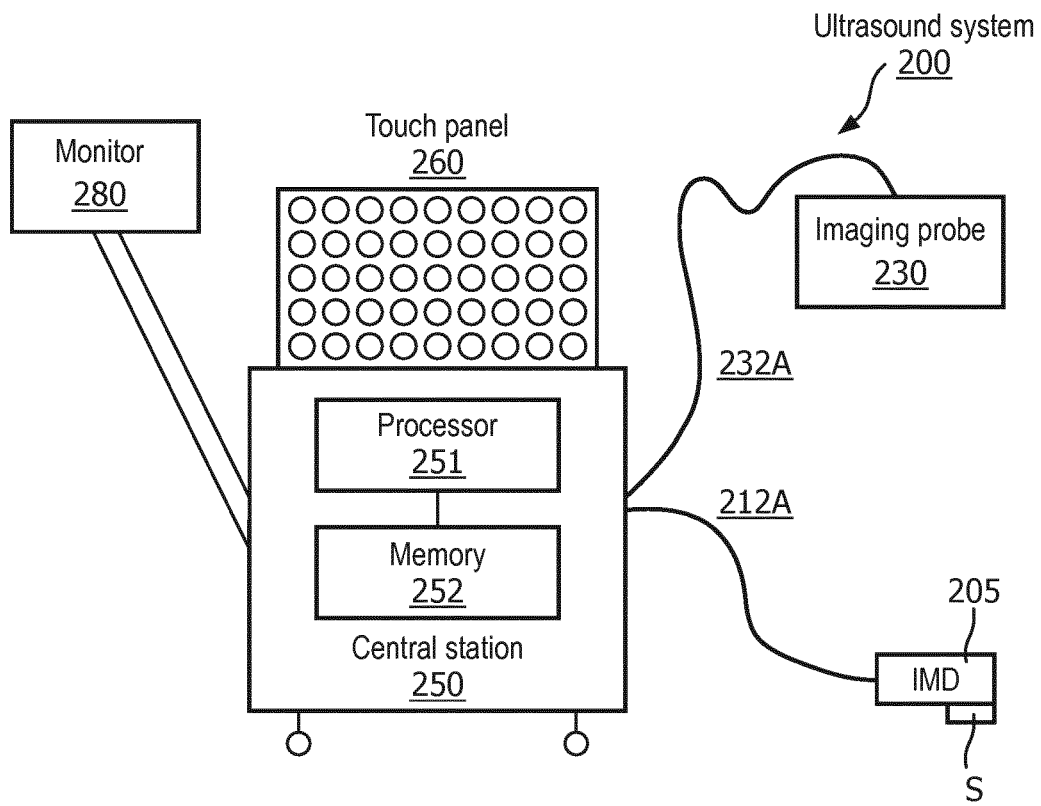
FIG. 2A illustrates an ultrasound system for noise reduction for ultrasound operations, in accordance with a representative embodiment.

In FIG. 2A, an ultrasound system 200 includes a central station 250 with a processor 251 and memory 252, a touch panel 260, a monitor 280, an imaging probe 230 connected to the central station 250 by wire 232A, and an interventional medical device 205 (IMD) connected to the central station 250 by wire 212A. The imaging probe 230 is an ultrasound probe. A passive ultrasound sensor S is fixed to the interventional medical device 205, though the passive ultrasound sensor S may be fixed to one portion of the interventional medical device 205 and movable relative to another portion of the interventional medical device 205, such as when the passive ultrasound sensor S is fixed to a wire that moves within a sheath. The passive ultrasound sensor S can be, but does not necessarily have to be, provided at an extremity of any portion of the interventional medical device 205. Noise in the frequency bands used by InSitu mechanisms may be an object addressed by the noise reduction for ultrasound operations described herein. That is, noise reduction for ultrasound operations addresses noise in a frequency band used to determine location of the sensor S on the interventional medical device 205.

By way of explanation, the interventional medical device 205 is placed internally into a patient during a medical procedure. Locations of the interventional medical device 205 can be tracked using the passive ultrasound sensor S. The shape of each of the interventional medical device 205 and the passive ultrasound sensor S may vary greatly from what is shown in FIG. 2A and FIG. 2B.

For example, the passive ultrasound sensor S may receive ultrasound tracking beams to help determine a location of the passive ultrasound sensor S. Ultrasound tracking beams described herein may be ultrasound imaging beams that are otherwise used to obtain ultrasound images, or may be ultrasound tracking beams that are separate (e.g., separate frequencies, separate transmission timing) from the ultrasound imaging beams. The passive ultrasound sensor S may be used passively or actively to respond to the received ultrasound tracking beams. As described herein, ultrasound imaging beams and/or ultrasound tracking beams separate from the ultrasound imaging beams can be used to selectively, typically, or always obtain a location of the passive ultrasound sensor S. However, as also noted herein, the tracking can be performed using either or both of the ultrasound imaging beams or completely separate ultrasound tracking beams.

In FIG. 2A, wire 212A and wire 232A are used to connect the interventional medical device 205 and imaging probe 230 to the central station 250. For the imaging probe 230, a wire 232A may not present much of a concern, though the wire 232A may still be a distraction. For the interventional medical device 205, a wire 212A may be used to send back, for example, images when the interventional medical device 205 is used to capture images. However, a wire 212A may be of more concern in that the interventional medical device 205 is at least partly inserted in the patient. Accordingly, replacing the wire 232A and the wire 212A with wireless connections may provide some benefit.

Figure 2B:
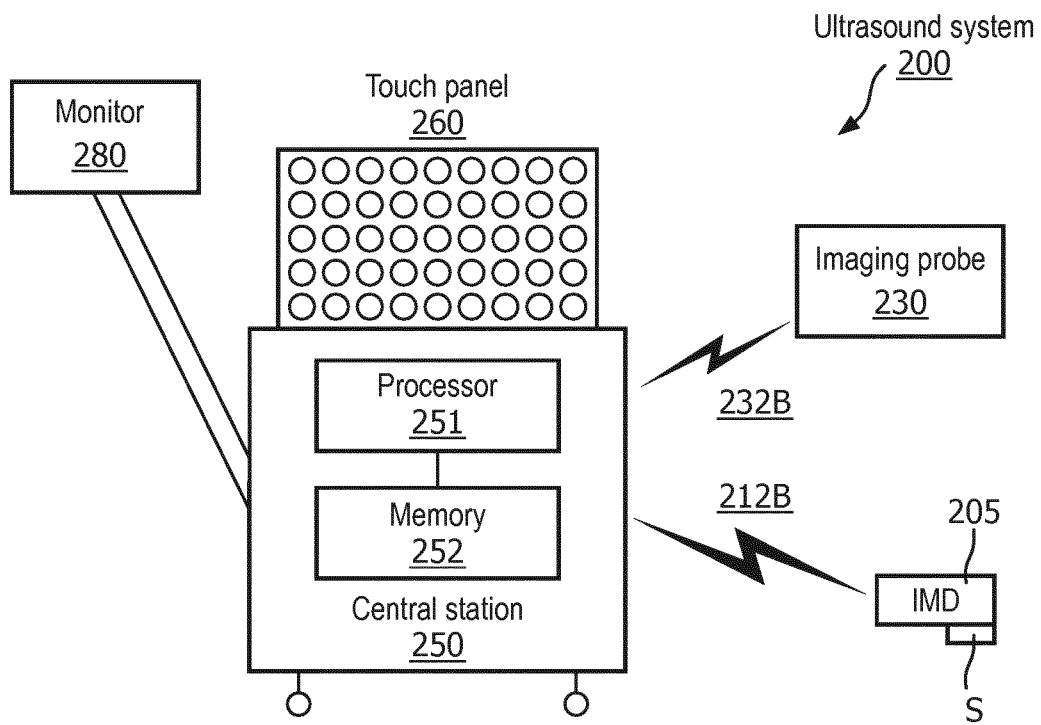
FIG. 2B illustrates another ultrasound system for noise reduction for ultrasound operations, in accordance with a representative embodiment.

FIG. 2B illustrates another ultrasound system for noise reduction for ultrasound operations, in accordance with a representative embodiment.

In FIG. 2B, the wire 232A is replaced with wireless data connection 232B, and the wire 212A is replaced with wireless data connection 212B. Otherwise, the ultrasound system 200 in FIG. 2B includes the same central station 250 as in FIG. 2A, i.e., with the processor 251 and memory 252, touch panel 260, monitor 280, imaging probe 230, and interventional medical device 205. The passive ultrasound sensor S moves with the interventional medical device 205.

In FIG. 2B, the ultrasound system 200 may be an arrangement with the interventional medical device 205 with the passive ultrasound sensor S on board. The interventional medical device 205 may include, e.g., a needle with the passive ultrasound sensor S at or near its tip. The passive ultrasound sensor S may also be configured to listen to and analyze data from tracking beams, such that the "sending" of the tracking beams from the imaging probe 230, and the "listening" to the tracking beams by the passive ultrasound sensor S, are synchronized. Use of tracking beams separate from imaging beams may be provided in an embodiment, but not necessarily the primary embodiment(s) of the present disclosure insofar as noise reduction for ultrasound operations primarily uses embodiments with only imaging beams.

In FIG. 2A or FIG. 2B, the imaging probe 230 may send a pulse sequence of imaging beams. An explanation of the relationship between the central station 250, imaging probe 230 and the passive ultrasound sensor S follows. In this regard, central station 250 in FIGS. 2A and 2B may include a beamformer (not shown) that is synchronized by a clock (not shown) to send properly delayed signals in a transmit mode to elements of an imaging array in the imaging probe 230. In a receive mode, the beamformer may properly delay and sum signals from the individual elements of the imaging array in the imaging probe 230. The ultrasound imaging itself is performed using the imaging probe 230, and may be in accordance with beamforming performed by the beamformer of the central station 250.

The imaging probe 230 may emit imaging beams as tracking beams that impinge on the passive ultrasound sensor S (i.e., when the passive ultrasound sensor S is in the field of view of the tracking beams). The passive ultrasound sensor S may receive and convert the energy of the tracking beams into signals so that the passive ultrasound sensor S, the interventional medical device 205, the imaging probe 230 or the central station 250 can determine the position of the passive ultrasound sensor S relative to the imaging array of the imaging probe 230. The relative position of the passive ultrasound sensor S can be computed geometrically based on the received tracking beams received by the passive ultrasound sensor S.

Thus, the imaging probe 230 emits tracking beams to the interventional medical device 205 for a period of time that includes multiple different points of time. For example, tracking beams may be emitted for 30 seconds, 60 seconds, 120 seconds, 180 seconds or any other period of time that include multiple different points of time. The tracking beams may be emitted by the imaging probe 230 in an ordered combination of time of emission and angle of emission relative to the imaging probe 230 (ultrasound probe). Energy of the tracking beams (imaging beams) may be collected periodically as responses to the imaging beams, such as every second or every $\frac{1}{10}$th second. The responses to the tracking beams may be reflected energy reflected by the passive ultrasound sensor S. Alternatively, the responses to the tracking beams may be active signals generated by the passive ultrasound sensor S, such as readings of the received energy of the tracking beams. Based on the responses to the tracking beams, the processor 251 may determine, for example, absolute position of the passive ultrasound sensor S at multiple different points in time during a period of time.

The central station 250 may be considered a control unit or controller that controls the imaging probe 230. As described in FIGS. 2A and 2B, the central station 250 includes a processor 251 connected to a memory 252. The central station 250 may also include a clock (not shown) which provides clock signals to synchronize the imaging probe 230 with the passive ultrasound sensor S. Moreover, one or more elements of the central station 250 may individually be considered a control unit or controller. For example, the combination of the processor 251 and the memory 252 may be considered a controller that executes software to perform processes described herein.

The imaging probe 230 is adapted to scan a region of interest that includes the interventional medical device 205 and the passive ultrasound sensor S. Of course, as is known for ultrasound imaging probes, the imaging probe 230 also uses ultrasound imaging beams to provide images on a frame-by-frame basis. The imaging probe 230 can also use separate tracking beams to obtain the location of the passive ultrasound sensor S.

In a one-way relationship, the passive ultrasound sensor S may be adapted to convert tracking beams provided by the imaging probe 230 into electrical signals. The passive ultrasound sensor S may be configured to provide either the raw data or partially or completely processed data (e.g., calculated sensor locations) to the central station 250, either directly or indirectly (e.g., via a transmitter or repeater located in a proximal end of the interventional medical device 205). These data, depending on their degree of processing, are either used by the central station 250 to determine the location of the passive ultrasound sensor S (and the location of the distal end of the interventional medical device 205 to which the passive ultrasound sensor S is attached), or to provide the central station 250 with the location of the passive ultrasound sensor S (and the location of the distal end of the interventional medical device 205 to which the passive ultrasound sensor S is attached).

As described herein, the positions of the passive ultrasound sensor S are determined by or provided to the central station 250. The positions of the passive ultrasound sensor S can be used by the processor 251 to overlay the positions of the passive ultrasound sensor S onto an image frame for display on the monitor 280.

Broadly, in operation, the processor 251 initiates a scan by the imaging probe 230. The scan can include emitting imaging beams as tracking beams across a region of interest. The imaging beams are used to form an image of a frame; and as tracking beams to determine the location of the passive ultrasound sensor S. As can be appreciated, the image from imaging beams is formed from a two-way transmission sequence, with images of the region of interest being formed by the transmission and reflection of subbeams. Additionally, in a one-way relationship, the imaging beams act as tracking beams incident on the passive ultrasound sensor S and may be converted into electrical signals (i.e., rather than or in addition to reflecting the tracking beams). In a two-way relationship, the imaging beams as tracking beams are reflected by the passive ultrasound sensor S, so that the imaging probe 230 determines the location of the passive ultrasound sensor S using the reflected tracking beams.

As noted above, data used to determine locations of the passive ultrasound sensor S may be or include raw data, partially processed data, or fully processed data, depending on where location is to be determined. Depending on the degree of processing, these data can be provided to the processor 251 for executing instructions stored in the memory 252 (i.e., of the central station 250) to determine the positions of the passive ultrasound sensor S in the coordinate system of ultrasound images from the beamformer. Alternatively, these data may include the determined positions of the passive ultrasound sensor S in the coordinate system which is used by the processor 251 when executing instructions stored in the memory 252 to overlay the position of the passive ultrasound sensor S on the ultrasound image in the monitor 280. To this end, the beamformer of the central station 250 may process the beamformed signal for display as an image of a frame. The output from the beamformer can be provided to the processor 251. The data from the passive ultrasound sensor S may be raw data, in which case the processor 251 executes instructions in the memory 252 to determine the positions of the passive ultrasound sensor S in the coordinate system of the image; or the data from the passive ultrasound sensor S may be processed by the passive ultrasound sensor S, the interventional medical device 205, or the imaging probe 230 to determine the locations of the passive ultrasound sensor S in the coordinate system of the image. Either way, the processor 251 is configured to overlay the positions of the passive ultrasound sensor S on the image on the monitor 280. For example, a composite image from the imaging beams as tracking beams may include the image of tissue and actual or superposed positions of the passive ultrasound sensor S, thereby providing real-time feedback to a clinician of the position of the passive ultrasound sensor S (and the distal end of the interventional medical device 205).

Figure 3:
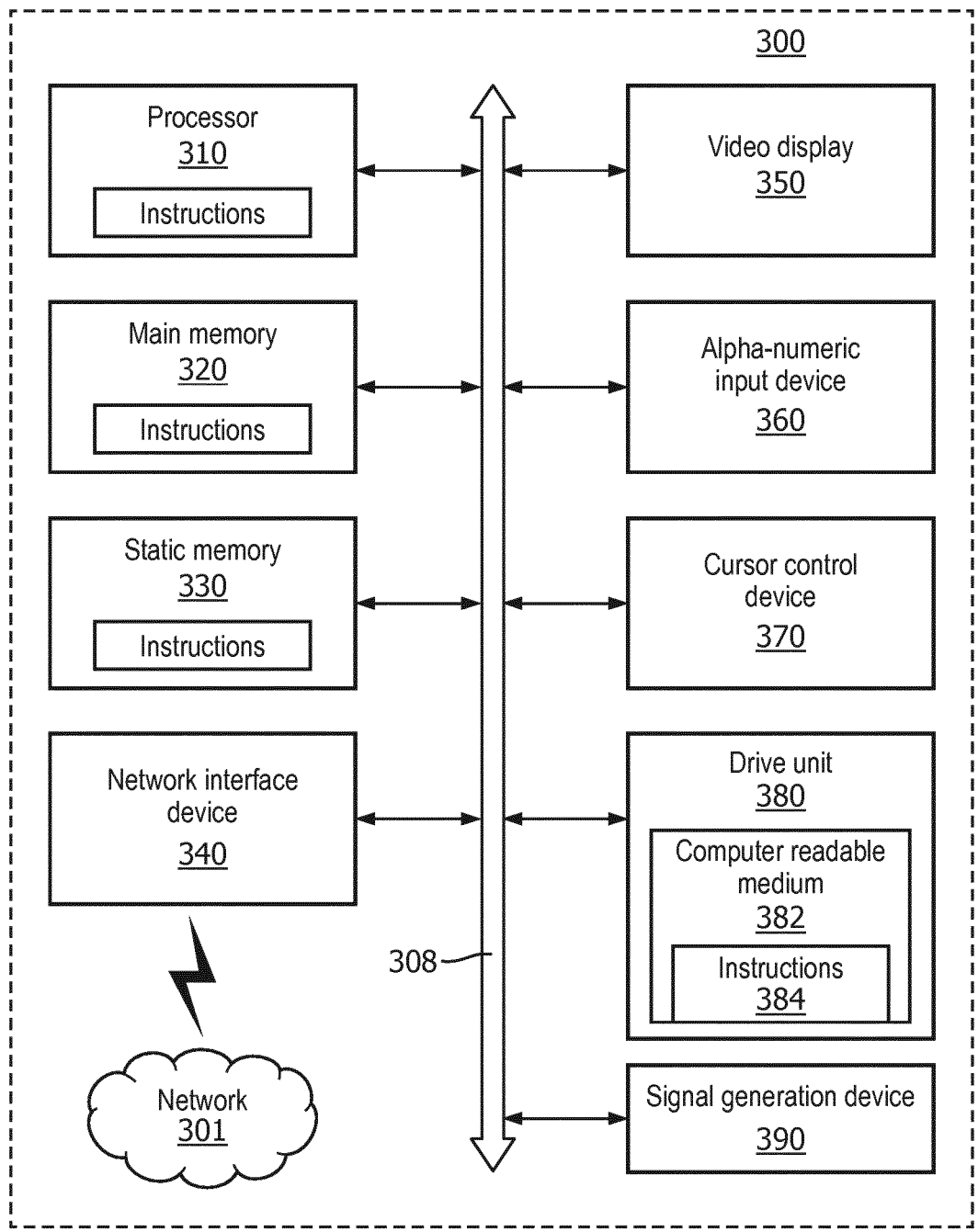
FIG. 3 is an illustrative embodiment of a general computer system, on which a method of noise reduction for ultrasound operations can be implemented, in accordance with a representative embodiment.

FIG. 3 is an illustrative embodiment of a general computer system, on which a method of noise reduction for ultrasound operations can be implemented, in accordance with a representative embodiment.

The computer system 300 can include a set of instructions that can be executed to cause the computer system 300 to perform any one or more of the methods or computer based functions disclosed herein. The computer system 300 may operate as a standalone device or may be connected, for example, using a network 301, to other computer systems or peripheral devices.

The computer system 300 can be implemented as or incorporated into various devices, such as a stationary computer, a mobile computer, a personal computer (PC), a laptop computer, a tablet computer, an ultrasound system, an ultrasound probe, a passive ultrasound sensor S, an interventional medical device 205, an imaging probe 230, a central station 250, a controller, or any other machine capable of executing a set of instructions (sequential or otherwise) that specify actions to be taken by that machine. The computer system 300 can be incorporated as or in a device that in turn is in an integrated system that includes additional devices. In an embodiment, the computer system 300 can be implemented using electronic devices that provide voice, video or data communication. Further, while the computer system 300 is illustrated as a single system, the term "system" shall also be taken to include any collection of systems or sub-systems that individually or jointly execute a set, or multiple sets, of instructions to perform one or more computer functions.

As illustrated in FIG. 3, the computer system 300 includes a processor 310. A processor for a computer system 300 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A processor is an article of manufacture and/or a machine component. A processor for a computer system 300 is configured to execute software instructions to perform functions as described in the various embodiments herein. A processor for a computer system 300 may be a general-purpose processor or may be part of an application specific integrated circuit (ASIC). A processor for a computer system 300 may also be a microprocessor, a microcomputer, a processor chip, a controller, a microcontroller, a digital signal processor (DSP), a state machine, or a programmable logic device. A processor for a computer system 300 may also be a logical circuit, including a programmable gate array (PGA) such as a field programmable gate array (FPGA), or another type of circuit that includes discrete gate and/or transistor logic. A processor for a computer system 300 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 300 includes a main memory 320 and a static memory 330 that can communicate with each other via a bus 308. Memories described herein are tangible storage mediums that can store data and executable instructions, and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 300 may further include a video display unit 350, such as a liquid crystal display (LCD), an organic light emitting diode (OLED), a flat panel display, a solid-state display, or a cathode ray tube (CRT). Additionally, the computer system 300 may include an input device 360, such as a keyboard/virtual keyboard or touch-sensitive input screen or speech input with speech recognition, and a cursor control device 370, such as a mouse or touch-sensitive input screen or pad. The computer system 300 can also include a disk drive unit 380, a signal generation device 390, such as a speaker or remote control, and a network interface device 340.

In an embodiment, as depicted in FIG. 3, the disk drive unit 380 may include a computer-readable medium 382 in which one or more sets of instructions 384, e.g. software, can be embedded. Sets of instructions 384 can be read from the computer-readable medium 382. Further, the instructions 384, when executed by a processor, can be used to perform one or more of the methods and processes as described herein. In an embodiment, the instructions 384 may reside completely, or at least partially, within the main memory 320, the static memory 330, and/or within the processor 310 during execution by the computer system 300.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 382 that includes instructions 384 or receives and executes instructions 184 responsive to a propagated signal; so that a device connected to a network 101 can communicate voice, video or data over the network 301. Further, the instructions 384 may be transmitted or received over the network 301 via the network interface device 340.

Figure 4A:
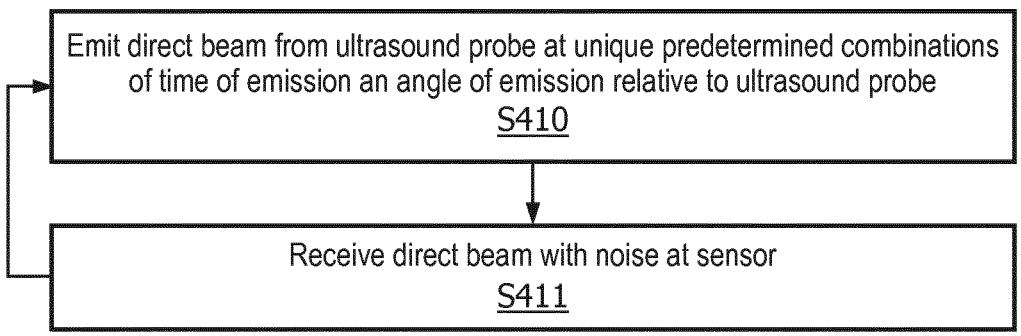
FIG. 4A illustrates a process for noise reduction for ultrasound operations, in accordance with a representative embodiment.

FIG. 4A illustrates a process for noise reduction for ultrasound operations, in accordance with a representative embodiment.

In FIG. 4A, only two steps are shown. At S410, an imaging probe 230 (ultrasound probe) emits a imaging beam at a unique predetermined combination of time of emission and angle of emission relative to the imaging probe 230 (ultrasound probe). At S411, a sensor S on an interventional medical device 205 receives the imaging beam with noise. The process of FIG. 4A repeats until a predetermined pattern of predetermined combinations of time of emission and angle of emission is completed, or until the predetermined pattern is interrupted or changed by an operator.

In FIG. 4A, two periods are of interest, a first time from when the imaging beam is emitted at S410 to when the imaging beam is received at S411, and a second time from when the imaging beam is received at S411 to when the next imaging beam is emitted at S410. The first time and the second time may each be considered a period such as a window.

As described herein, strong outside electromagnetic interference signals (EMI) that prevent tracking in an InSitu tracking system is often repetitive, and can be coupled into InSitu hardware with a magnitude that fluctuates slowly in time, depending on, for example, the position of the clinician relative to the noise source. Noise reduction for ultrasound operations provides a nonlinear filtering mechanism to reduce the detrimental effects of such signals on the tracking performance. EMI interference can be suppressed in InSitu raw data of sections that are used such as the periods from S410 to S411, by analyzing sections that are thrown away such as the periods from S411 to S410. In the thrown away data there should be not intended acoustic signal, only interference and noise, and autocorrelation searching of characteristics of signals can be used to find the repetition rate and interference locations. This interference location pattern can then be extrapolated into the used data from the periods from S410 to S411, and locations where potential EMI interference is predicted to occur can be interpolated using the 2D/3D neighboring (timewise) sensor signal. Noise reduction for ultrasound operations provides a 'spatial' interference prediction method that works even on very broad band EMI that would otherwise be hard to suppress using standard methods such as Wiener filtering.

In FIG. 4A, repetitive noise may be identified from times when the imaging beams are reflected from the passive ultrasound sensor S on the interventional medical device 205 as reflected beams at S411 to when the reflected beams are received by the imaging probe 230 (ultrasound probe) at S410, but not from times when the imaging beams are emitted by the imaging probe 230 (ultrasound probe) to the passive ultrasound sensor S on the interventional medical device 205 at S410 to when the imaging beams are reflected from the passive ultrasound sensor S at S5411. In other words, sensor readings during the transmit stage from S410 to S411 may be ignored, whereas sensor readings during the receive stage from S411 to S410 may be considered since theoretically the imaging probe 230 should be receiving the reflected imaging beams and the passive ultrasound sensor S should not be receiving a signal other than noise during the receive stage from S411 to S410.

To be clear, the periods from S410 to S411 and S411 to S410 may not correspond exactly to the stated emission, reflections and receipt. Rather, the periods may include be shorter or longer than the exact times between the stated emission, reflections and receipt. What is being described, however, is that noise may be identified during times when the imaging probe 230 (ultrasound probe) is not emitting imaging beats between S411 to S410, as this is when noise is isolated. Of course, noise may be identified during both periods in an embodiment, as the noise can be approximated by filtering out the energy of the emitted beams received by the passive ultrasound sensor S.

The predetermined pattern may be preset and stored by the central station 250, or the imaging probe 230. The imaging probe 230 may analyze signals returned from the most recent emitted imaging beam at the time from S411 to the next emission at S410, or may provide raw data or processed data to the central station 250. Additionally, the passive ultrasound sensor S may perform some level of logical analysis of the imaging beam received by the passive ultrasound sensor S.

Figure 4B:
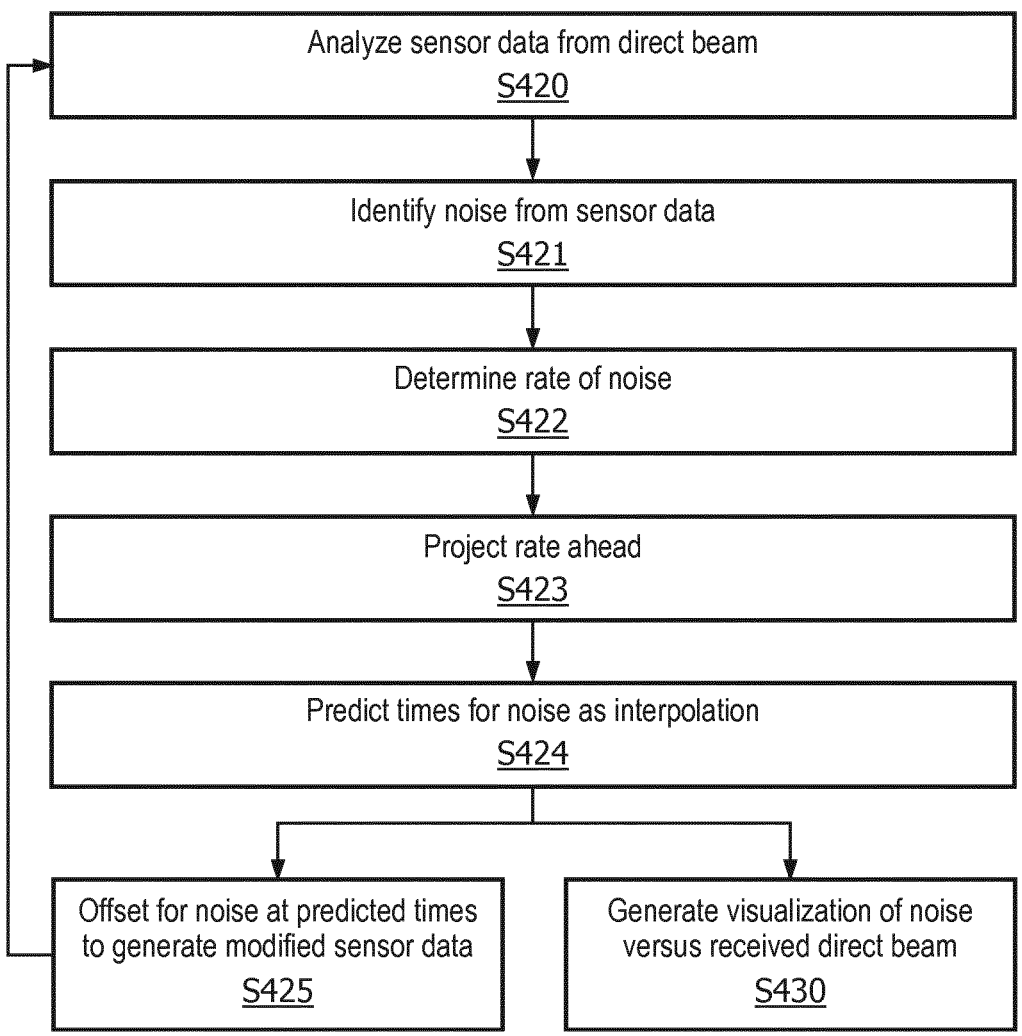
FIG. 4B illustrates another process for noise reduction for ultrasound operations, in accordance with a representative embodiment.

FIG. 4B illustrates another process for noise reduction for ultrasound operations, in accordance with a representative embodiment.

At S420, sensor data from the imaging beam received by the passive ultrasound sensor S is analyzed. The raw data may be analyzed by the passive ultrasound sensor S, such as to determine the intensity of the signal, and the results may be returned to the central station 250 for additional analysis as described herein. Alternatively, the raw data may be provided directly from the passive ultrasound sensor S to the central station 250 for analysis as described herein.

At S421, noise is identified from the analysis of the passive ultrasound sensor data at S420. That is, the ultrasound system 200 will know what signal is supposed to be received by the passive ultrasound sensor S based on knowledge of the time of emission and angle of emission of the imaging beam at S410, as well as the identified location of the passive ultrasound sensor S from the InSitu processing.

As an example, characteristics of beams received as signals at the sensor S may be analyzed to automatically identify the repetitive noise by correlating characteristics of the signals that include the repetitive noise from a first source. After the noise from the first source is offset as described below, the analysis may be performed again to automatically identify the repetitive noise by correlating characteristics of the signals that include the repetitive noise from a second source.

At S422, a rate of the noise identified at S421 is determined. The noise may be identified from repetitions within a single cycle from S410 to S411 and back to S410, or over multiple cycles of dozens, hundreds or thousands of such cycles. The noise may be strictly periodic, or may repeated at a discernible pattern that is not strictly periodic, such as by a pattern that slows and weakens by a set amount or percentage each occurrence.

At S423, the rate of the noise is projected ahead. That is, by identifying a pattern of times when the noise has occurred, the pattern can be projected ahead. Times at which the repetitive noise is identified can be extrapolated into the future based on the rate of noise identified at S422 and the timings of the passive ultrasound sensor readings at S422. In other words, the process of FIG. 4 may involve extrapolating from times at which the repetitive noise from a first source is received during the times when the imaging beams are reflected from the passive ultrasound sensor S on the interventional medical device 405 at S411, to times at which the repetitive noise from the first source is received during the times when the imaging beams are emitted by the imaging probe 230 (ultrasound probe) to the passive ultrasound sensor S at S410 on the interventional medical device 405 at S410. Thus, the extrapolating at S423 may be from repetitive noise identified in a second signal set from S411 to S410 when imaging beams are not received, to a first signal set from S410 to S411 when the imaging beams are received.

In an alternative to the embodiment of FIG. 4B, noise may be identified from both the first period and the second period, so from times when the imaging beams are reflected from the passive ultrasound sensor S on the interventional medical device 405 as reflected beams to when the reflected beams are received by the imaging probe 230 (ultrasound probe), as well as from times when the imaging beams are emitted by the imaging probe 230 (ultrasound probe) to when the imaging beams are reflected from the passive ultrasound sensor S as reflected beams. In other words, in the alternative embodiment, noise may be identified from when imaging beams are received at the sensor S, as well as from when imaging beams are not received by the sensor S and only noise should be present.

At S424, times for the noise to occur is predicted ahead as an interpolation. The predicting of repetitive noise from the first source at S424 may be based on the extrapolating/extrapolation at S423 described above. The predictions will therefore cover noise that can be expected to accompany the transmit signal from the imaging probe 230 (ultrasound probe). That is, each instance of noise may be predicted ahead, so that noise can be offset in either period from S410 to S411 when imaging beams are emitted, as well as from S410 to S411 when imaging beams are not emitted. As a reminder, the noise of concern in noise reduction for ultrasound operations is primarily external noise that is generated independent of the ultrasound system 200 but which still affects ultrasound operations such as InSitu processing.

At S425, the noise can be offset at the predicted times, such as by cancelling or reducing the noise using active noise control (ANC) or active noise reduction (ANR) which involves adding a second sound designed to cancel the first. Alternatively, if the noise mainly affects data processing, the data can be adjusted by an amount to offset the predicted amounts at each predicted time. The result of S425 is modified sensor data to reflect removal or cancellation of the noise that is offset. That is, noise is removed at predicted times at S425.

At S430, the method of FIG. 4 generates a visualization of the noise versus the received imaging beam received at the passive ultrasound sensor S. The visualization at S420 may be performed simultaneous with, before, or after the offsetting at S425. After S425, the process may return to S420 to analyze the sensor data for more noise that may have been present.

The visualization at S430 may include generating a spatialized representation of signals received at the imaging probe 230 (ultrasound probe) that include repetitive noise identified in repetitive noise identification from the first source. Spatialized representations of signals are shown in FIGS. described below. The visualization at S430 may also include segregating the spatialized representation into a first group that includes (all) signals received at the passive ultrasound sensor S, and a second grouping that includes signals from the first source. The autocorrelating of characteristics of signals described herein may be performed by correlating the characteristics in the second grouping. Furthermore, the offsetting described herein may be performed by offsetting elements of the spatialized representation in the first grouping, i.e., in the grouping that includes energy from imaging beams as well as energy from noise.

The visualization at S430 may also involve isolating a first signal set of the signal data that includes the repetitive noise (e.g., from a first source or from multiple sources) and the signals based on the imaging beams received at the passive ultrasound sensor S, from a second signal set that includes the repetitive noise but not the signals based on the imaging beams received at the passive ultrasound sensor S. Moreover, supplemental analysis may be used to identify a peak of acoustic intensity (activity) in the first signal set after the offsetting, to check whether additional noise is present.

Figure 5:
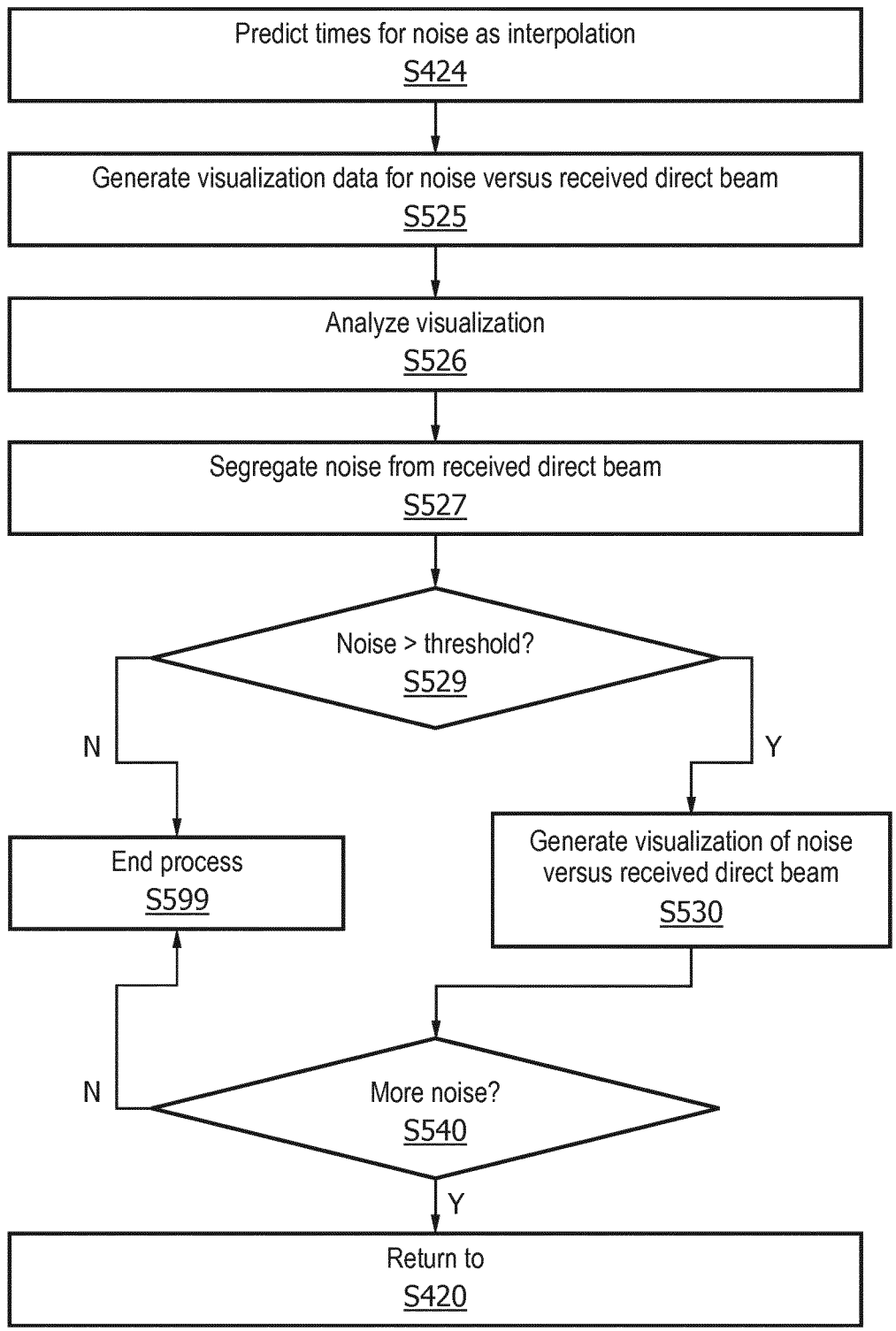
FIG. 5 illustrates another process for noise reduction for ultrasound operations, in accordance with a representative embodiment.

FIG. 5 illustrates another process for noise reduction for ultrasound operations, in accordance with a representative embodiment.

The process of FIG. 5 includes activities between the time from the prediction of times at S424 to the generation of visualizations at S430 in FIG. 4, as well as activities after the generation of the visualizations at S430 in FIG. 4. In FIG. 5, S430 is relabeled S530, but is otherwise substantively the same.

At S424, the process in FIG. 5 begins with the prediction of noise locations (times) as predicted noise locations for noise as an interpolation. The noise locations are identified based on repetitive noise identification described herein. At S525, visualization data is generated for noise versus the received imaging beam received at S411. The visualization data may be generated by reshaping a sequence of intensity readings at S411 into two-dimensional (2D). For example, the visualization data may be the intensity readings versus time, or versus each corresponding beam since the imaging beams are emitted one at a time. The two-dimensional data may include depth reflective of imaging beam propagation, and identification of a corresponding imaging beam among the imaging beams. That is, the depth may be depth reflective of imaging beam propagation via the imaging beams.

At S526, the visualization is analyzed. For example, the visualization may be compared with projected readings that show expected intensities for each beam. The analysis at S526 may be an image analysis, or the equivalent logical exercise of analyzing the visualization data from S525.

At S527, noise is segregated from the received imaging beam. For example, the noise intensity may be visualized separate from the imaging beam intensity, or the noise intensity may be visualized separately from the combination of the imaging beam intensity and the noise intensity. The noise may be segregated by subtracting the expected intensity reading for an imaging beam received by the passive ultrasound sensor S. Alternatively, as described herein, the passive ultrasound sensor S may be read when no imaging beam is expected, as any intensity recorded should be noise.

At S529, the noise is compared to a threshold, such as a predetermined threshold used to determine when noise is consequential enough to remove or reduce. If the noise is not above the threshold (S529=No), the process ends at S599. If the noise is above the threshold (S529=Yes), the visualization of the noise is generated versus the received imaging beam at S530. The visualization of noise signals versus the received imaging beam signals at S530 may include one view of the received imaging beam combined with the noise, another view of the noise in isolation, and another view of the received imaging beam in isolation.

At S540 an analysis is performed to determine whether more noise exists after the offsetting of the noise at S425. The analysis performed at S540 may be performed to determine when multiple different independent noise sources affect operations of the ultrasound system 200. If more noise is present even after the offsetting at S425 and the visualization at S530 (S540=Yes), the process returns to S420 to again analyze the sensor data, now modified with the offsetting from the previous iteration or iterations of S425 for previously identified noise.

Figure 6:
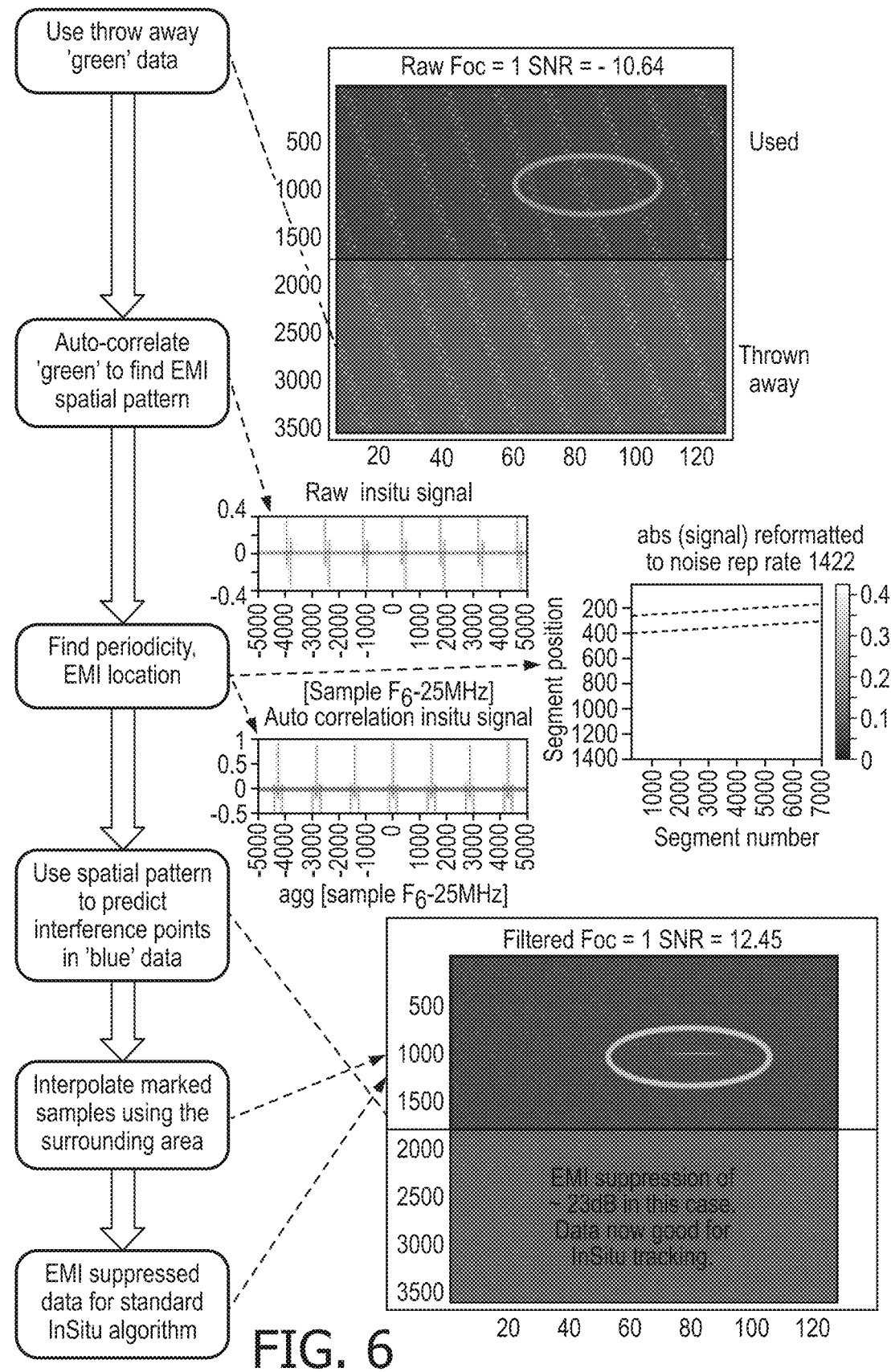
FIG. 6 illustrates a process for reshaping of sensor location data in noise reduction for ultrasound operations, in accordance with a representative embodiment.

FIG. 6 illustrates a process for reshaping of sensor location data in noise reduction for ultrasound operations, in accordance with a representative embodiment.

The InSitu data coming from the passive ultrasound sensor S can be reshaped as shown in FIG. 6. In FIG. 6, the vertical axis is time/depth and the horizontal axis is beam number. To find the location of the passive ultrasound sensor S, the peak of the acoustic intensity 'blob' in FIG. 6 needs to be determined, but this is hindered by the presence of repetitive noise shown by the diagonal features in FIG. 6. The depth in the reshaped data in FIG. 6. is reflective of imaging beam propagation.

The beam-to-beam timing is determined by the 2-way travel time of the desired imaging depth. In the example of FIG. 6, 3500 samples are taken, but for InSitu the signal does not have to be reflected, which means that one half (½) of the time can be used to analyze noise without expecting a received imaging beam. Thus, the relevant InSitu signal in FIG. 6 is only the 1750 samples which are shown in the top half labelled "Used", and the 1750 samples in the bottom half labelled "Thrown away" will only have noise and interference because the imaging beam from the imaging probe 230 has passed the passive ultrasound sensor S. The 1750 samples in the bottom half labelled "Thrown away" are converted back into a time vector with voids (missing time segments) where the data for the top 1750 samples would be. An auto correlation procedure can find the repetition rate and locations of the repetitive interference pattern from the 1750 samples in the bottom half labelled "Thrown away".

For illustrative purposes, an example method is shown on the left in FIG. 6 consistent with the description above. Here, the sensor signal is reshaped according to the repetition rate found with an autocorrelation search for characteristics of signals, making the interference show up as horizontal line features for the charts in the middle of FIG. 6. All the pixels corresponding to the horizontal lines are labeled, and the data reshaped back to InSitu format, resulting in the predicted interference points in the data for the top 1750 samples (labelled "Used") being marked. The pattern of the marked samples in the bottom right figure will look similar to the diagonal dotted lines in the top right figure, and will have a distributed dotted quality that lends itself to interpolation by surrounding pixels. In an embodiment, the pattern in the marked samples in the bottom right figure may have larger dot sizes to enhance robustness for interference jitter. These marked samples can then be interpolated using the surrounding data. Note that this surrounding data also comes from adjacent InSitu beams that are not 'neighbors' in the time domain but do belong to the same acoustic feature.

In the process on the left side of FIG. 6, the bottom 1750 samples labelled "Thrown away" are used. Autocorrelation is performed to find the EMI spatial pattern, and periodicity is found along with EMI locations. The EMI spatial pattern is then used to predict noise and interference in the top 1750 samples labelled "Used". The marked samples are interpolated using the surrounding area, and the EMI suppressed data are made available for the standard InSitu algorithm. As shown, an improvement of approximately 23 dB was obtained using the processing of FIG. 6, corresponding to processing for image data, or processing of data that is suitable for imaging.

Figure 7:
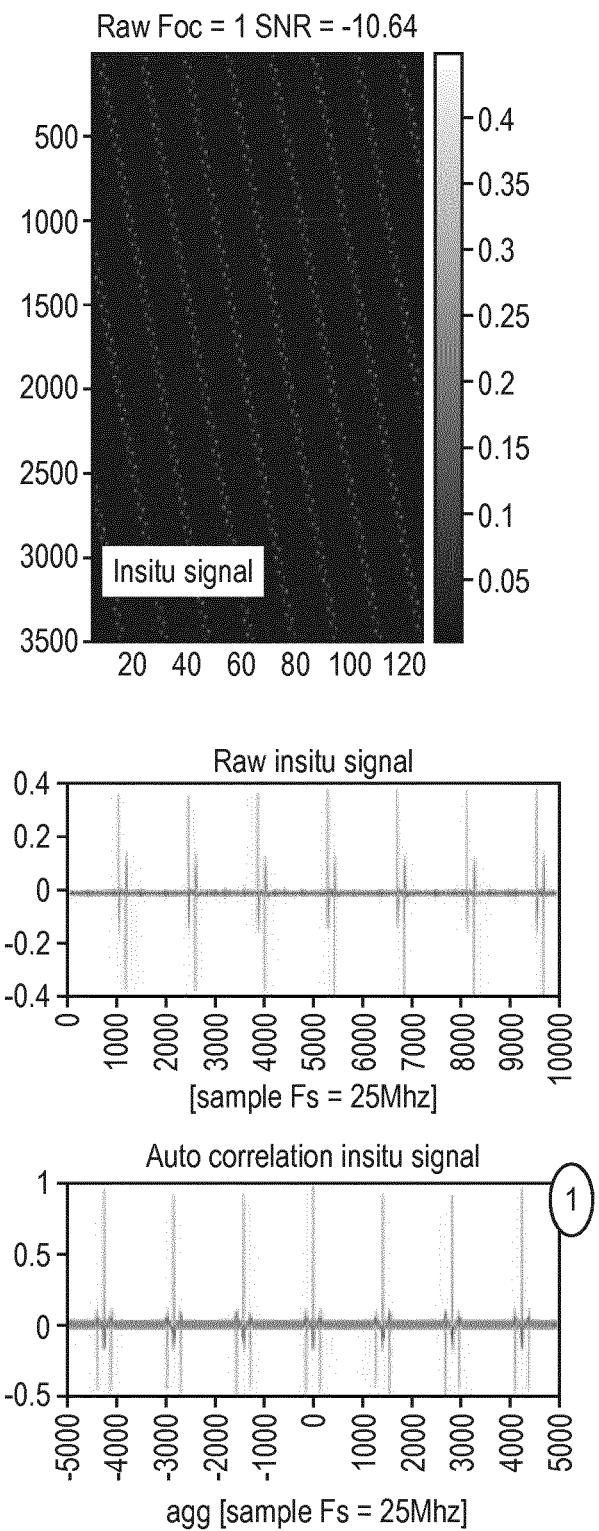
FIG. 7 illustrates another process for reshaping of sensor location data in noise reduction for ultrasound operations, in accordance with a representative embodiment.
Figure 7:
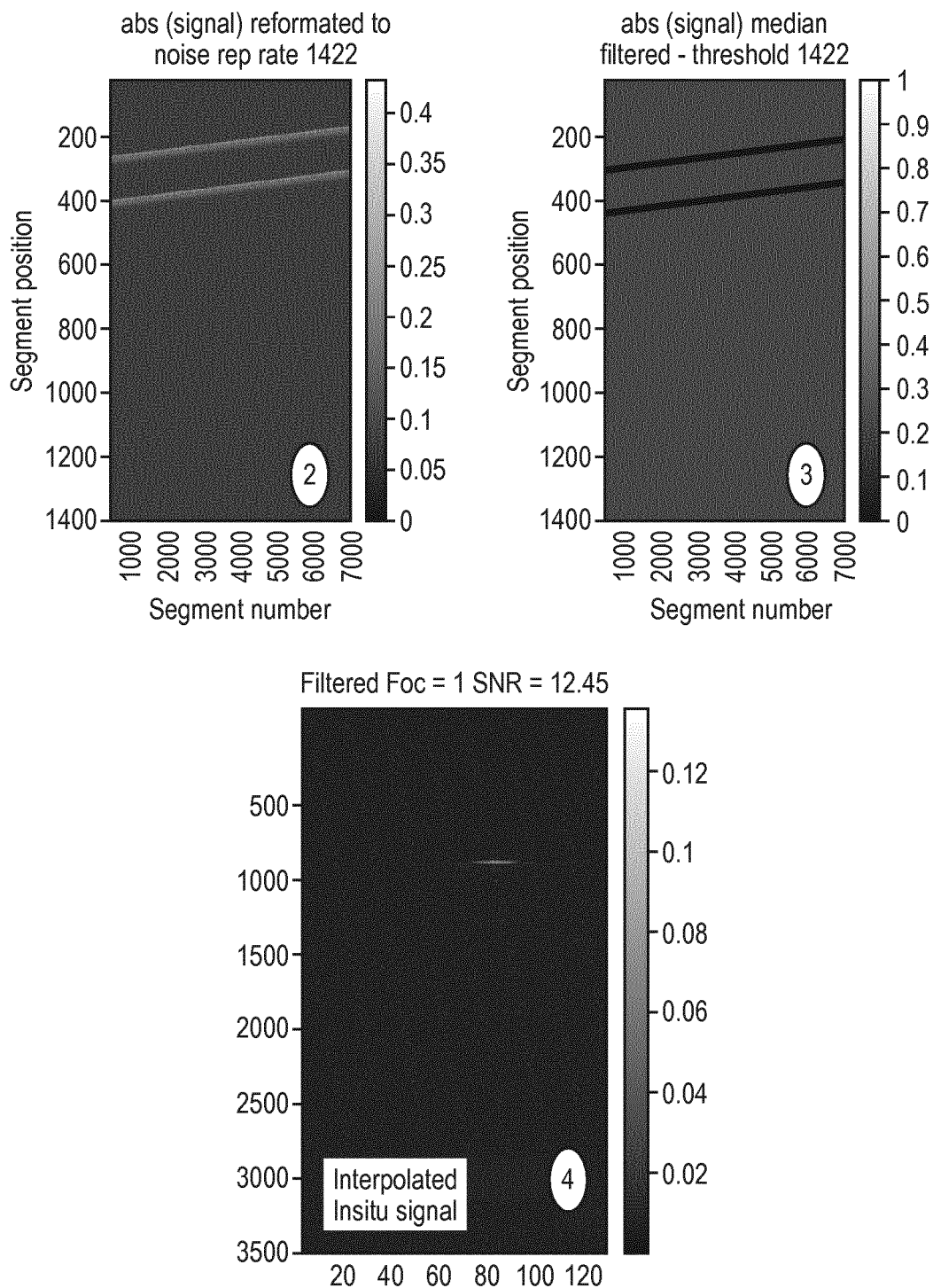

FIG. 7 illustrates another process for reshaping of sensor location data in noise reduction for ultrasound operations, in accordance with a representative embodiment.

In FIG. 7, a time window of raw InSitu sensor signal is analyzed in Step 1 using autocorrelation among characteristics of signals. The autocorrelation peak spacing reveals a repetition rate slightly less than 1422 samples. In Step 2, the noise pattern is aligned by reshaping to this repetition rate of slightly less than 1422 samples. Note that because the repetition rate is not exactly 1422 samples, the interference feature is not exactly horizontal but has a slight slope. As the auto correlation analysis is performed over a large time window (100 k+ samples), the repetition rate is known at subsample precision, and the slope of this interference feature is known. Note that these interference lines are not necessarily solid lines, as depending on the clinical situation the interference gets coupled in at varying degrees.

In Step 3, a horizontal projection is performed along the known interference feature angle, and with a threshold on that profile, the locations of the interference are determined. Where an interference threshold on the profile is exceeded, a label is back projected along the interference angle onto the 2D matrix. Optionally, the labelled line can be thickened slightly to allow for additional jitter in the interference signal to also be filtered out.

Note that for the data in the matrix we can use only the "Thrown away" green section that only has noise and interference but no imaging beams, and zero out the blue area corresponding to imaging beams to avoid acoustic events that would influence interference detection. Alternatively, if interference heavily dominates acoustic events then all data can be used, as having twice as much interference signal available for detection may outweigh the (small) chance of the acoustic events perturbing the interference detection. In Step 4, the labelled data is reshaped into InSitu format and interference regions interpolated.

Figure 8:
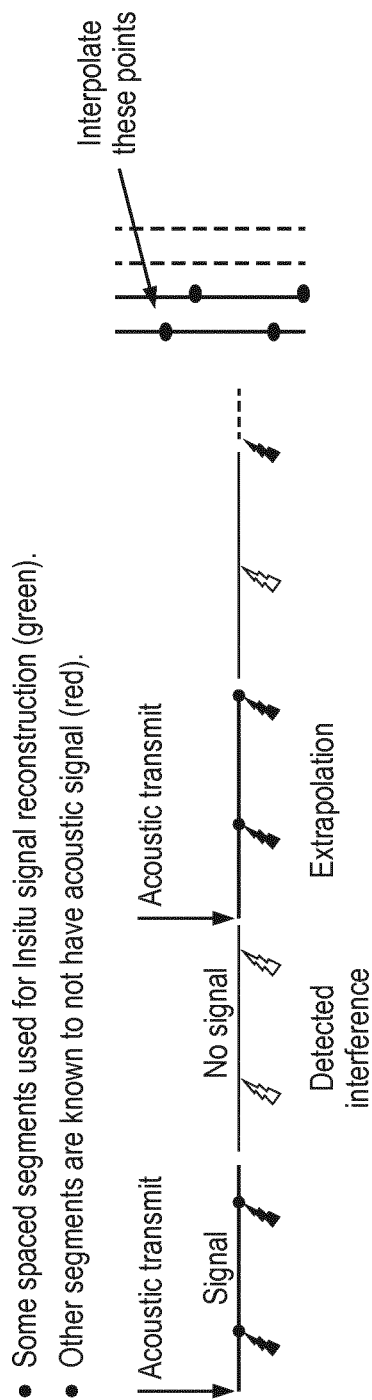
FIG. 8 illustrates a process for filtering in noise reduction for ultrasound operations, in accordance with a representative embodiment.

FIG. 8 illustrates a process for filtering in noise reduction for ultrasound operations, in accordance with a representative embodiment.

A high-level description of noise reduction for ultrasound operations is provided in FIG. 8. For FIG. 8, the filtering principle is applicable for a 'raster type' signal that is corrupted by periodic interference. Additional advantages can be gained when a priory known time windows exist where it is known that no signal is present but interference signals are still produced.

The descriptions for FIGS. 2-8 above are for specific embodiments, to better illustrate principles. In an actual implementation one would, for example, probably not rearrange data into physical matrices, but use pointer arithmetic instead to achieve the same purpose. One may also use circular buffers, sliding windows, and re-use calculations made earlier. The size of the sliding time window for these calculations will depend on how stationary and strong the interference pattern is, and could change adaptively.

The choice of what data to use to analyze the interference (All signal, or only No signal segments) can also be made adaptively. If the acoustic signal from the passive ultrasound sensor is fairly confined spatially (in plane sensor, low reverb), it is advantageous to use All signal, as the acoustic signals will not cause a significant change in the autocorrelation function of the signal. If the acoustic signal is more distributed, with many peaks due, for example, to reverberations, there is a risk that the autocorrelation may pick up a repetitive signature related to an acoustic phenomenon. In this case it may be better to only use the 'no signal' sections for the interference analysis. This requires a modified autocorrelation function that ignores contribution from data points in the signal sections.

A standard formula for discrete auto correlation is shown as equation (1) below:

$$y(k) = \frac{\sum_{n=1}^{N-K} x(n)x(n+k)}{\sum_{n=1}^{N-K} x(n)^2} \quad (1)$$

In equation (1), x(n) is the digitized sensor signal, k is the lag, and N is the size of the time window used for calculations. For noise reduction for ultrasound operations, the range for k should be sufficiently large to capture the repetition rate of the interference signal, and N should be much larger than k. If all data is used, equation (1) is applied as shown. On the other hand, if only data of the no signal portion in the embodiment of FIG. 8 is used, the summations in equation (1) do not take place over the whole n=1 to N−K range but only over those values of n where both x(n) and x(n+k) belong to the no signal portion.

In the event of encountering multiple independent periodic interference sources, noise reduction for ultrasound operations can solve the period interference using an iterative approach. For example, noise reduction for ultrasound operations may first perform autocorrelation, then the fast fourier transform (FFT) of the result can be taken, and the frequency component of the largest component analyzed to filter out the noise source. By iteratively repeating the process, the next noise source can be filtered, until there are no interference patterns left that exceed the autocorrelation threshold. Accordingly, noise from a first source can be removed, and subsequent processing can remove noise from a second source. The noise from the second source may occur at a rate different than the noise from the first source, and may warrant different analysis and visualization of signals as described herein.

Figure 9:
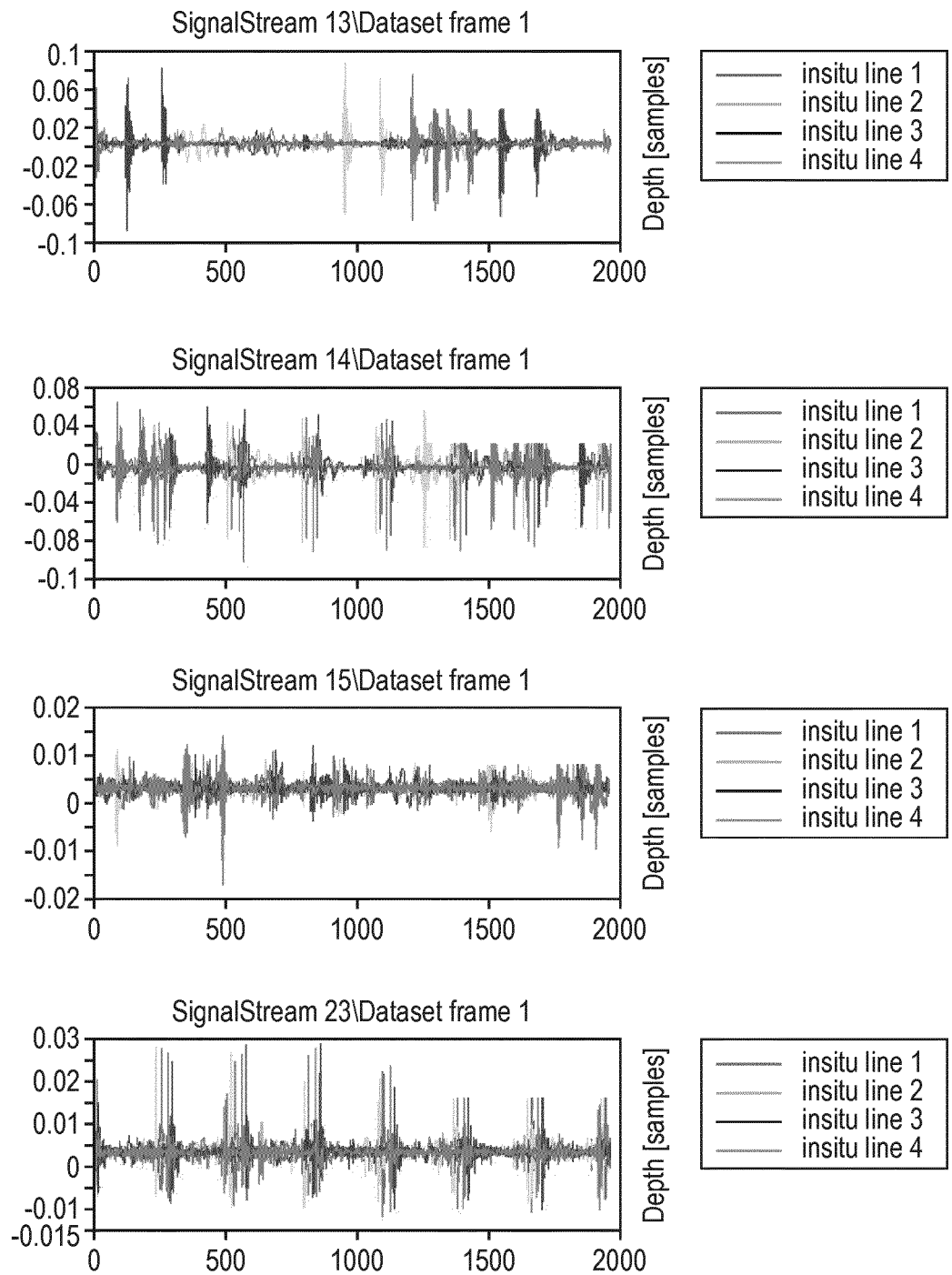
FIG. 9 illustrates noise signals collected in noise reduction for ultrasound operations, in accordance with a representative embodiment.
Figure 9:
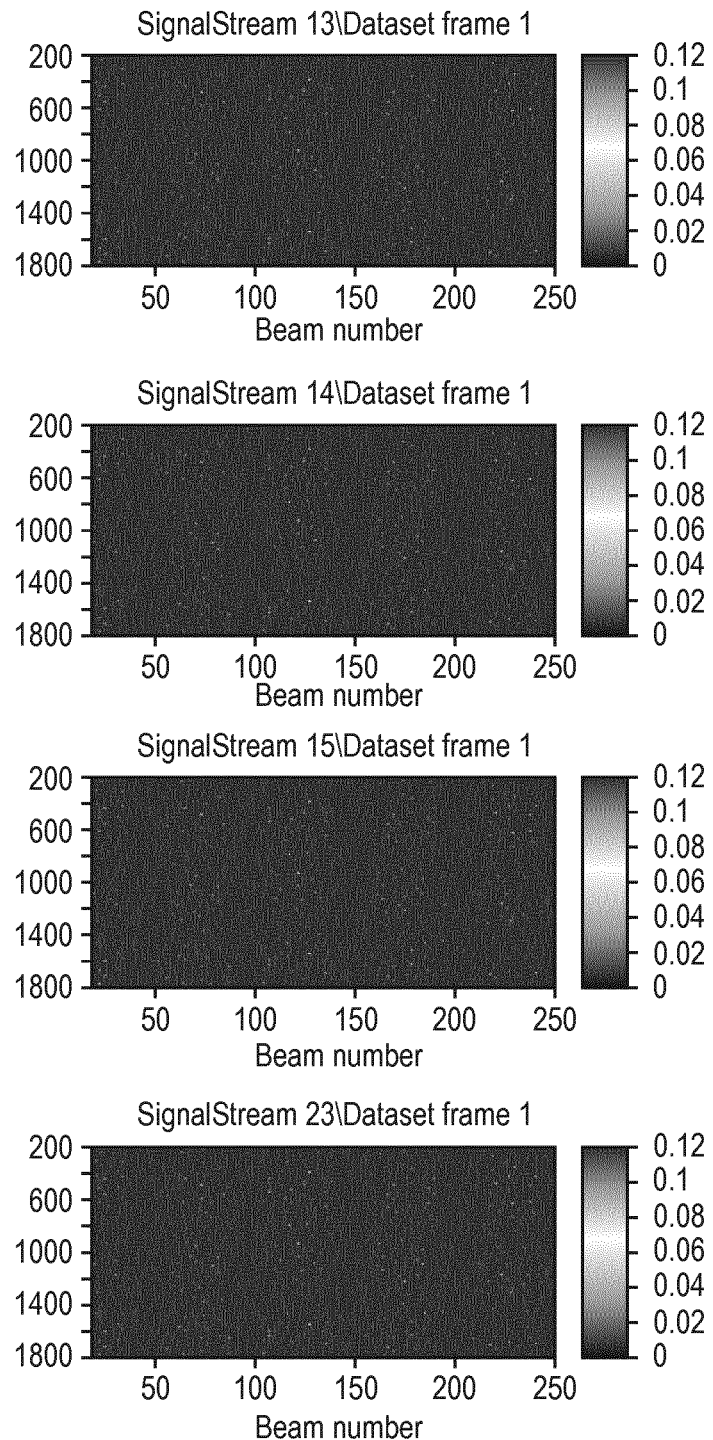
Figure 9:
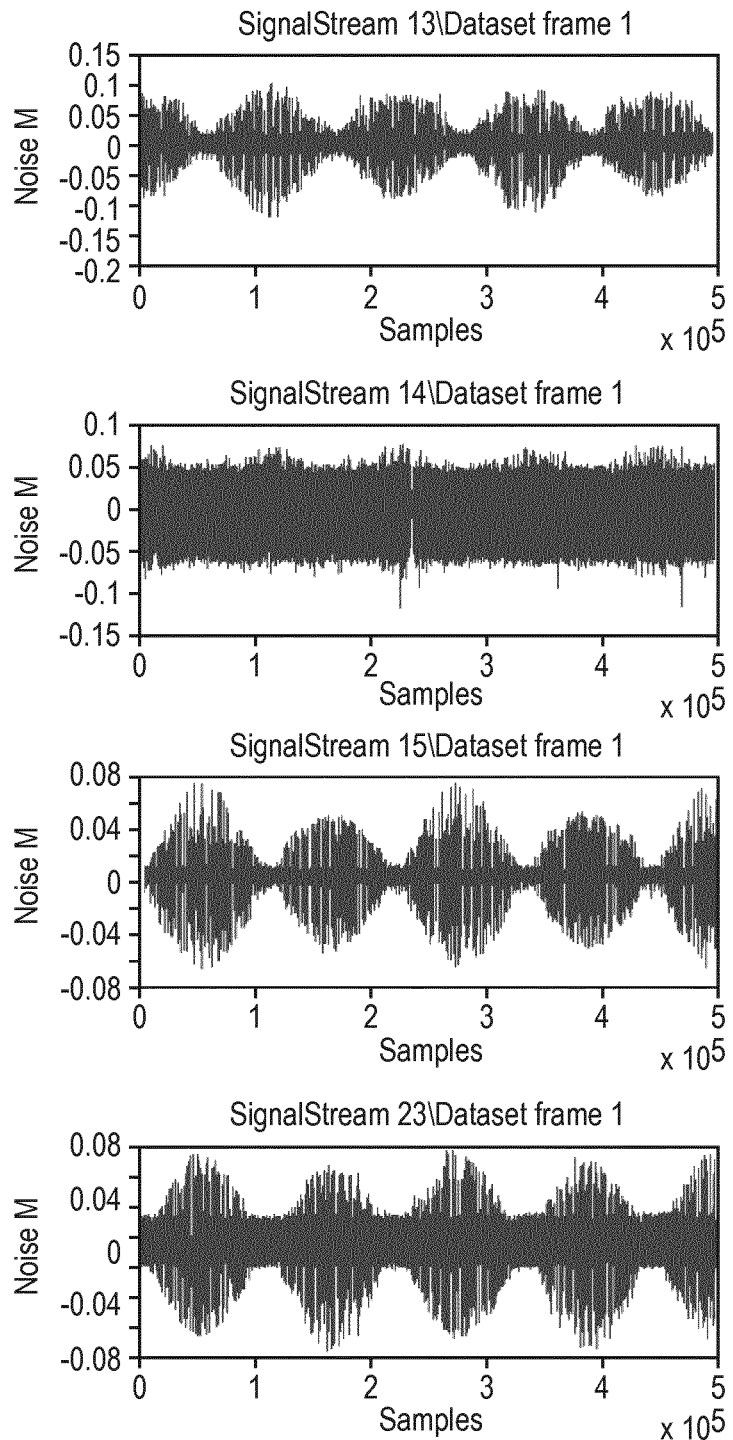

FIG. 9 illustrates noise signals collected in noise reduction for ultrasound operations, in accordance with a representative embodiment.

In FIG. 9, the noise signals shown in the charts were collected during an animal experiment. The noise to be reduced is from a PC monitor. In FIG. 9, four rows each show a different moment in time with the operator (person) operating the system doing different things, and the imaging probe 230 facing away from the passive ultrasound sensor S so only noise is captured. The first (left) column shows 4 InSitu lines, with a repetitive noise pattern clearly visible. The second column shows one frame of raw InSitu data, wherein the noise is scattered but structured as noisy spikes.

The third (right) column shows the sensor signal over a larger time frame, where noise magnitude fluctuates with a rate of a few Hertz. The charts shown in FIG. 9 illustrate that highly repetitive noise sources can be encountered in a clinical setting, and can be addressed with noise reduction for ultrasound operations.

Figure 10:
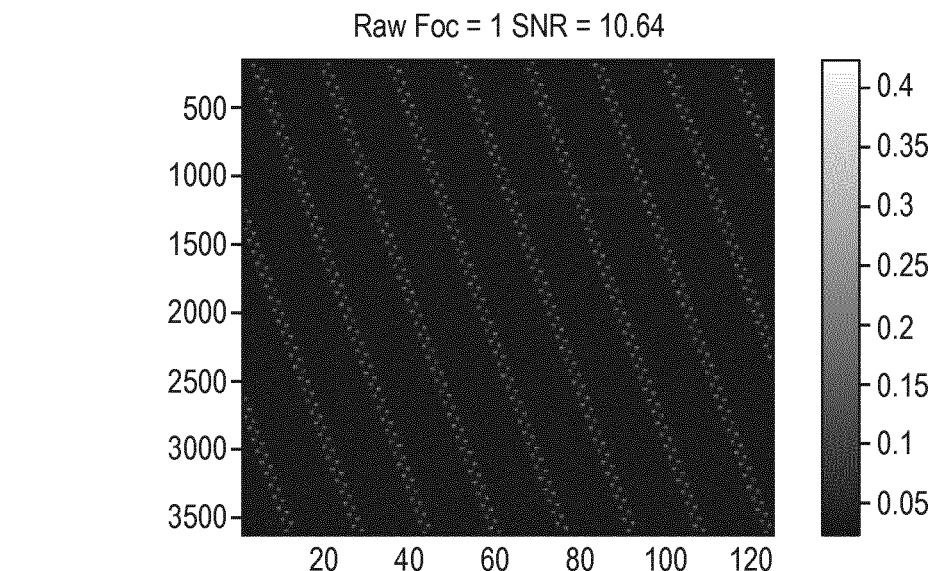
FIG. 10 shows operational results for noise reduction in ultrasound operations, in accordance with a representative embodiment.
Figure 10:
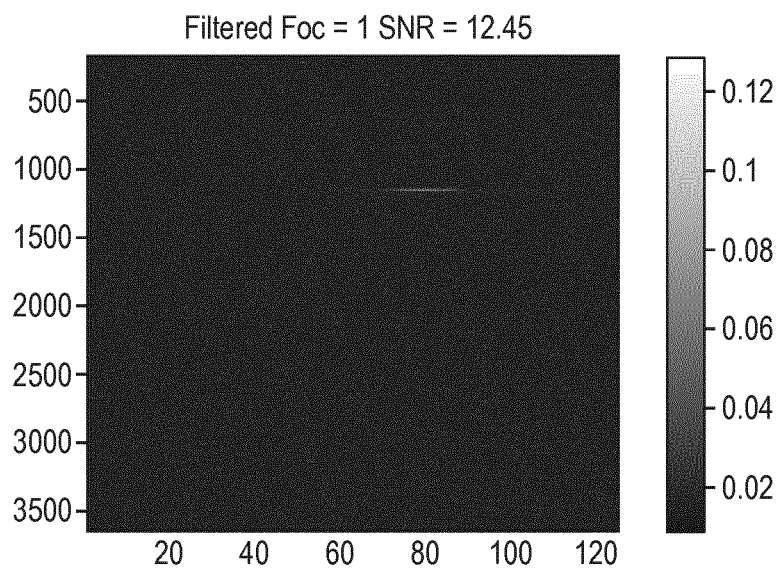

FIG. 10 shows operational results for noise reduction in ultrasound operations, in accordance with a representative embodiment.

In FIG. 10, an InSitu signal is shown before and after the filtering described above for noise reduction in ultrasound operations. At the time of animal experiments described for FIG. 9, the InSitu tracking data (blue area) was saved, and the unused data (green) was not available. However, a noise source was recreated in a laboratory with a programmable waveform generator that has the same structure as the noise observed in the animal experiments, and the entire set of time data was collected from the passive ultrasound sensor while tracking a needle in a water tank. Note that the interference pattern was suppressed by 23 dB without significantly affecting the signal of interest, even though some of the interference was spatially overlapping the signal of interest.

Accordingly, noise reduction for ultrasound operations enables quieter and more accurate ultrasound operations. Noise reduction for ultrasound operations may be proofed by injecting periodic interference in only one part of the transmit/receive cycle, such as in a transmit (signal) segment, and comparing the result with injecting periodic interference continuously in all segments. Noise reduction for ultrasound operations can also be proofed by injecting a largely periodic interference where there is only an infrequent timing deviation, wherein the interference is suppressed where there are no timing deviations, but left untouched at every timing deviation. Finally, noise reduction for ultrasound operations can be proofed by injecting temporally periodic interference with a large magnitude and spectrum fluctuation, as these fluctuations should not affect performance for the noise reduction for ultrasound operations methods described above.

Noise reduction for ultrasound operations can be used for a variety of systems, including InSitu tracking systems, analog 'raster' type signals such as video, ultrasound, CT, radar, and lidar.

Although noise reduction for ultrasound operations has been described with reference to several exemplary embodiments, it is understood that the words that have been used are words of description and illustration, rather than words of limitation. Changes may be made within the purview of the appended claims, as presently stated and as amended, without departing from the scope and spirit of noise reduction for ultrasound operations in its aspects. Although noise reduction for ultrasound operations has been described with reference to particular means, materials and embodiments, noise reduction for ultrasound operations is not intended to be limited to the particulars disclosed; rather noise reduction for ultrasound operations extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A system for determining location of an interventional medical device within a patient, the system comprising:
   a sensor at a location on the interventional medical device;
   an ultrasound probe configured to emit a plurality of beams, wherein signals, comprising the plurality of beams emitted by the ultrasound probe and repetitive noise, are received at the sensor; and
   a controller comprising a processor coupled to memory, the processor configured to:
      analyze the signals received at the sensor and identify the repetitive noise in the signals, wherein the processor is configured to identify the repetitive noise by an autocorrelation search of characteristics of the signals that determines a repetitive noise pattern comprising a repetitive rate and locations of the repetitive noise, offset the repetitive noise in the signals by interpolating locations in the signals based on the repetitive noise pattern, and determine the location of the interventional medical device based on the offset signals.

2. The system of claim 1, wherein the processor is further configured to:

identify the repetitive noise during a period from reflection of the plurality of beams from the sensor to receipt of the reflected beams by the ultrasound probe.

3. The system of claim 2, wherein the processor is further configured to:

extrapolate based on receipt of the repetitive noise at the sensor during the period from reflection of the plurality of beams from the sensor to receipt of the reflected beams by the ultrasound probe and based on receipt of the repetitive noise at the sensor during a period from emission of the plurality of beams by the ultrasound probe to reflection of the plurality of beams from the sensor.

4. The system of claim 3, wherein the processor is further configured to:

predict, based on the extrapolation, the repetitive noise during a second period from emission of the plurality of beams by the ultrasound probe to the sensor to reflection of the plurality of beams from the sensor, and remove the predicted repetitive noise from signals during the second period.

5. The system of claim 4, wherein the instructions, when executed by the processor, further cause the processor to:

use a frequency band of the removed repetitive noise to determine the location of the sensor on the interventional medical device.

6. The system of claim 1, wherein the processor is further configured to:

identify the repetitive noise during a period from reflection of the plurality of beams from the sensor to receipt of the reflected beams by the ultrasound probe, and identify the repetitive noise during a period from emission of the plurality of beams by the ultrasound probe to reflection of the emitted plurality of beams from the sensor.

7. The system of claim 1, wherein the processor is further configured to:

compare the repetitive noise to a threshold to determine whether to interpolate the signals.

8. The controller system of claim 1, wherein the processor is further configured to:

identify second repetitive noise received with the plurality of beams at the sensor, interpolate second signals based on the plurality of beams received at the sensor, and offset the second repetitive noise at locations of the second repetitive noise in the second signals.

9. The system of claim 1, wherein the processor is further configured to:

generate a spatialized representation of signals received at the ultrasound probe that include the repetitive noise;

segregate the spatialized representation into a first grouping that includes signals received at the sensor and a second grouping that includes noise signals;

automatically identify the repetitive noise by correlating characteristics in the second grouping to determine the repetitive noise pattern; and offsetting elements of the spatialized representation in the first grouping based on the repetitive noise pattern.

10. The system of claim 1, wherein the processor is further configured to:

reshape signal data from the sensor into two-dimensional data comprising depth reflective of imaging beam propagation and identification of a corresponding beam among the plurality of beams;

isolate a first signal set of the signal data that includes the repetitive noise and the signals received at the sensor from a second signal set of the signal data that includes the repetitive noise but not the signals received at the sensor;

offset the repetitive noise in the first signal set by interpolating predicted noise locations from the first signal set, wherein the predicted noise locations are predicted based on repetitive noise identification in the second signal set and extrapolation from the repetitive noise identification in the second signal set to the first signal set; and identify a peak of acoustic intensity in the first signal set after offsetting the repetitive noise in the first signal set.

* * * * *